United States Patent [19]

Bailey

[11] Patent Number: 4,585,764

[45] Date of Patent: Apr. 29, 1986

[54] GASTRIC CYTOPROTECTION WITH 3,3'-THIOBIS[PROPANOIC ACID] IN ORAL ADMINISTRATION OF ASPIRIN

[75] Inventor: Denis M. Bailey, East Greenbush, N.Y.

[73] Assignee: Sterling Drug Inc., New York, N.Y.

[21] Appl. No.: 725,448

[22] Filed: Apr. 22, 1985

[51] Int. Cl.$^4$ ............................................. A61K 31/61
[52] U.S. Cl. .................................................... 514/163
[58] Field of Search ................................ 514/163, 164

[56] References Cited

U.S. PATENT DOCUMENTS

| | | | |
|---|---|---|---|
| 2,579,679 | 12/1951 | Leffler | 514/561 |
| 3,988,466 | 10/1977 | Takagi et al. | 514/561 |
| 4,016,268 | 4/1977 | Goldenberg et al. | 514/561 |
| 4,491,574 | 1/1985 | Seifter et al. | 514/561 |

OTHER PUBLICATIONS 3,3'-Thiobis[propanoic acid], The Merck Index, Tenth Edition, 1983, item 9172, p. 1336.

*Primary Examiner*—Stanley J. Friedman
*Attorney, Agent, or Firm*—Robert K. Bair; B. Woodrow Wyatt; Paul E. Dupont

[57] ABSTRACT

The method of providing cytoprotection of the gastric mucosa in a mammal receiving aspirin (ASA) perorally which comprises orally administering either prior to or in combination with ASA a cytoprotectively effective amount of 3,3'-thiobis[propanoic acid] (TBPA) or in combination with a pharmaceutically acceptable carrier. Also shown is a composition for providing cytoprotection of the gastric mucosa in a mammal receiving ASA perorally which comprises ASA in combination with a cytoprotectively effective amount of TBPA.

19 Claims, No Drawings

GASTRIC CYTOPROTECTION WITH 3,3'-THIOBIS[PROPANOIC ACID] IN ORAL ADMINISTRATION OF ASPIRIN

BACKGROUND OF THE INVENTION a. Field of the Invention

This invention relates to gastric cytoprotection in oral administration of aspirin.

b. Information Disclosure Statement

Takagi et al in U.S. Pat. No. 3,988,466, issued Oct. 26, 1977, show that gastric lesions induced by aspirin or indomethacin are prevented by administration of amino acids, in particular, L-glutamine, L-lysine and L-arginine.

Goldenberg et al in U.S. Pat. No. 4,016,268, issued Apr. 5, 1977, show that bismuth subsalicylate co-administered with aspirin or other antiinflammatory drugs combats gastric ulceration associated with such drugs.

Seifter et al in U.S. Pat. No. 4,491,574, issued Jan. 1, 1985 show the use of the vitamin A or precursor thereof in a method of reducing toxicity and inhibiting ulcerogenesis and bleeding in the stomach of a mammal due to the ingestion of aspirin. This reference also cites a number of other publications pertaining to various means for inhibiting the gastric ulcerogenic effects of aspirin or other antiinflammatory agents, e.g., indomethacin.

3,3'-Thiobis[propanoic acid], as shown in The Merck Index, Tenth Edition, 1983, item 9172, page 1336, is said to be used as an antioxidant for soap products and polymers of ethylene, used in plasticizers and lubricants, and proposed for use in edible fats, oils and other foods.

Leffler in U.S. Pat. No. 2,579,679, issued Dec. 25, 1951, shows the use of thiodipropionic acid, same as 3,3'-thiobis[propanoic acid], as a stabilizing agent for vitamin $B_{12}$ in aqueous solution.

SUMMARY OF THE INVENTION

In a method aspect the invention resides in the method of providing cytoprotection of the gastric mucosa in a mammal receiving aspirin perorally which comprises orally administering either prior to or in combination with aspirin a cytoprotectively effective amount of 3,3'-thiobis[propanoic acid] alone or in combination with a pharmaceutically acceptable carrier.

In another method aspect the invention resides in the method of preventing or inhibiting gastric lesions in a mammal receiving aspirin perorally which comprises orally administering either prior to or in combination with aspirin a cytoprotectively effective amount of 3,3'-thiobis[propanoic acid] alone or in combination with a pharmaceutically acceptable carrier.

In a composition aspect the invention resides in a composition for providing cytoprotection of the gastric mucosa in a mammal receiving aspirin perorally which comprises aspirin in combination with a cytoprotectively effective amount of 3,3'-thiobis[propanoic acid].

DETAILED DESCRIPTION INCLUSIVE OF PREFERRED EMBODIMENTS

Various studies or experiments were carried out to demonstrate the effectiveness of 3,3'-thiobis[propanoic acid] as a gastric cytoprotective agent in said method aspects of the invention. Fasted Sprague-Dawley female rats were given intragastrically (ig) at least three different doses ranging from 5-30 mg/100 g body weight of 3,3'-thiobis[propanoic acid] either 30 minutes before or parallel with intragastric administration of 10 mg/100 g body weight of acidified aspirin. Rats were killed one hour after aspirin (ASA) administration and the number of hemorrhagic gastric erosions (or lesions) was determined and the area of erosion was measured by computerized planimetry. 3,3'-Thiobis[propanoic acid] (TBPA) co-administered with ASA was found to offer significant ($p<0.01$) gastric cytoprotection, the minimum effective dose being about 30 mg/100 g. The effectiveness of TBPA as cytoprotectant against ASA-induced gastric lesions was also demonstrated in arthritic rats using the standard pharmacological antiinflammatory adjuvant-induced arthritis assay wherein it also was established that TBPA did not reduce the antiinflammatory efficacy of ASA. Also, it was shown that coadministration of TBPA with ASA did not affect the bioavailability of ASA, and, further, that TBPA and the coadministered combination thereof with ASA had a low order of toxicity.

Said composition aspect of the invention can be prepared by combining the ASA and TBPA alone or in combination with a pharmaceutically acceptable excipient carrier in conventional dosage forms such as capsules, tablets, caplets, and the like mixtures of these two ingredients being stable at room temperature and above, up to 50° C. or more, as shown hereinbelow. Said composition can be formulated in capsule form, e.g., a gelatin capsule, as a mixture of ASA and TBPA, said mixture alone or in combination with a pharmaceutically acceptable excipient, such as starch, silica or other conventional formulating excipient or additive. Alternatively and preferably, the ASA and TBPA can be formulated in tablet form by conventional means utilizing conventional formulating excipients or tabletting aids. It is contemplated that the ASA and TBPA can be formulated in controlled or sustained release form, for example, by encapsulating the particles of either or both in an appropriate conventional polymeric coating such as ethylcellulose or hydroxypropyl methylcellulose and then combining the encapsulated ASA and TBPA particles in combined dosage form either in gelatin capsules or in tablets formulated by conventional means.

Ordinarily the composition will contain from about 1 to about 3 parts by weight of TBPA per part of ASA, preferably about equal parts by weight the two ingredients. The actual weights of said ingredients per unit dosage form depend on the dosage of ASA to be administered. Therapeutically effective dosage amounts of ASA are of course well known in the art and range from about 80 mg. to about 1 g. The most common adult doses are 325 mg, 500 mg, and 650 mg and 1 g. Smaller doses, between about 80 to 325 mg, of course are used for children and in some instances larger doses may be used as an adult dosage.

In preparing in conventional manner tablets containing said ingredients, there may be incorporated prior to or during tabletting the conventional tabletting aids or excipients, such as binders, disintegrants, lubricants, plasticizers, diluents, colors, surfactants or wetting agents, and the like. Illustrative of these excipients are: binders—microcrystalline cellulose, lactose, sucrose; disintegrants—corn or potato starch, sodium starch glycolate; lubricants—magnesium stearate, talc, stearic acid, silicon dioxide; diluents—lactose, sucrose; plasticizers—glycerine, glyceryl triacetate, propylene glycol, polyethylene glycol 4000 or 6000; surfactants—sodium lauryl sulfate.

In carrying out the method aspect the ASA and TBPA can be coadministered using said composition aspect or the TBPA and ASA can be administered in separate unit dosage forms either simultaneously or sequentially, i.e., the TBPA followed by the ASA. Dosage regimen, i.e., frequency of administration, is well known in ASA therapy.

There follow examples and results which demonstrate the effectiveness of the method and composition aspects of the invention. Thus, the following test results are exemplary of the present ASA therapy improvement as applied to mammals and as demonstrated with rats. It is known to those skilled in the art of pharmaceutical chemistry that the experiments performed on animals as illustrated herein are indicative of corresponding effect in humans. The following examples will further illustrate the invention without, however, limiting it thereto.

EXAMPLE 1

Protection Against Aspirin-Induced Hemorrhagic Gastric Erosions and Mucosal Vascular Injury By 3,3'-Thiobis[propanoic Acid]

All of the experiments in this example were performed in female Sprague-Dawley rats having an initial body weight of 150–200 g. The animals housed under 12 hour light and dark cycles initially had an unlimited access to Purina ® laboratory chow and tap water. Before the administration of ASA, the rats were fasted overnight. Every group (control and experimental) consisted of 3–4 rats and each experiment was repeated at least twice and the results were pooled. The extent of gastric mucosal injury was evaluated by a Zeiss stereomicroscope coupled with a computerized planimeter which allowed both surface measurement and counting of lesions, according to the published method of Sandor Szabo et al entitled "A Quantitative Method for Assessing the Extent of Experimental Gastric Erosions and Ulcers", J. Pharmacological Methods 13, 59–66, 1985. Light microscopy of formalin-fixed sections was also performed.

ASA was suspended in 1% methylcellulose dissolved in 200 mM HCl and was administered at 10 mg/100 g body weight by gavage with rubber tube (Rusch No. 8) and rats were killed one hour later. The study design is presented as follows in Table A.

TABLE A
Study Design

Compound: 3,3'-Thiobis[propanoic Acid]
Doses: 0, 5, 10, 30 mg/100 g body weight
Time:
 Aspirin: 0 min.
 Compound: −30, −0.5 min.
 Autopsy: +60 min.

In the initial experiment, doses of TBPA were given per os (p.o.) either 30 minutes or 30 seconds before ASA. The 30 second pretreatment is virtually a parallel administration of the compounds. The intragastric gavage of ASA immediately followed the administration of the compound. In these experiments TBPA when given 30 minutes before aspirin exerted a dose-dependent protection against ASA-induced gastric erosions.

In the parallel administration protocol, the minimum statistically significant effective dose (MED) of TBPA was 30 mg/100 g on the basis of both area of lesions and number of lesions, as seen from Tables B and C, wherein the data are expressed respectively as percentage of glandular stomach area and as total number of erosions.

TABLE B
Effect of 3,3'-Thiobis[propanoic Acid] On Aspirin-induced Gastric Mucosal Erosions In Rats (Data expressed as percentage of glandular stomach area)

| Dose[a] | 0 | 5.0 | 10.0 | 30.0 |
|---|---|---|---|---|
|  | 1.20 | 0.71 | 0.44 | 0.05* |
| S.E | ±0.42 | ±0.35 | ±0.25 | ±0.03 |
| N | 9 | 9 | 9 | 9 |

[a]Single oral dose (mg/100 g body weight); ASA given concomitantly at 10 mg/100 g in acidified 1% methylcellulose and rats sacrificed 1 hour after drug administration.
*p <0.01

TABLE C
Effect of 3,3'-Thiobis[propanoic Acid] On Aspirin-induced Gastric Mucosal Erosions In Rats (Data expressed as total number of erosins)

| Dose[a] | 0 | 5.0 | 10.0 | 30.0 |
|---|---|---|---|---|
|  | 10.78 | 5.33 | 4.00* | 0.78* |
| S.E. | ±2.82 | ±2.06 | ±1.56 | ±0.43 |
| N | 9 | 9 | 9 | 9 |

[a]Single oral dose (mg/100 g body weight); ASA given concomitantly at 10 mg/100 g in acidified 1% methylcellulose and rats sacrificed 1 hour after drug administration.
*p ≦0.01

The above experiments indicate that coadministration of nontoxic doses of TBPA decrease or abolish ASA-induced gastric mucosal lesions.

EXAMPLE 2

Gastric Cytoprotection Against Aspirin Lesions In Adjuvant Arthritic Rats Using 3,3'-Thiobis[propanoic Acid]

Male Sprague-Dawley rats (initial weight of 280–353 g) received single oral daily doses of TBPA at either 150 or 300 mg/kg for 16 days coadministered with 150 mg/kg of ASA in an adjuvant-induced arthritis assay [C. J. Pearson, "Experimental Joint Disease", J. Chron. Dis. 16, 863–874 (1963); E. M. Glenn and J. Grey, "Adjuvant Induced Polyarthritis in Rats: Biologic and Histologic Background", Amer. J. Vet. Res. 26, 1180–1193 (1965)]. At the completion of the assay the stomachs were excised and examined for the presence or absence of lesions. Coadministration of TBPA at 150 mg/kg with 150 mg/kg of ASA resulted in fewer lesions (mean of 6.8), when compared with ASA alone (mean of 15.2); and, the mean size of the lesions was also reduced, being 5.57 mm$^2$ for TBPA with ASA compared with 16.02 mm$^2$ for aspirin alone. Coadministration of 300 mg/kg of TBPA with 150 mg/kg of ASA resulted in a mean number of lesions of 7.6 compared with a mean number of lesions of 25.7 for ASA alone; and, the mean size of the lesions was also reduced with coadministration of TBPA with ASA, being 5.28 mm$^2$ compared with 11.61 mm$^2$ for ASA alone. TBPA was effective in reducing the number and size of lesions induced with ASA when coadministered for 16 days at 150 and 300 mg/kg with ASA at 150 mg/kg, although it appeared that a plateau of effectiveness had been reached at the lower dose level of the TBPA. No enhancement of cytoprotective activity was determined at the higher dose level. Results of these studies are given below in Tables D and E.

TABLE D

Cytoprotection Against ASA Lesions In Adjuvant Arthritis Study

| Group (mg/kg)[a] | No. of Rats with Lesions | Area of Lesion (mm²) Mean + S.E. | No. of Lesions Mean + S.E. |
|---|---|---|---|
| Controls | 0/10 | 0 | 0 |
| ASA 150 | 10/10 | 16.02 ± 3.82 | 15.2 ± 2.9 |
| TBPA 150 | 0/5 | 0 | 0 |
| ASA 150 + TBPA 150 | 4/5 | 5.57 ± 2.90 | 6.8* ± 2.3 |

*Significantly different from control; p ≦0.05
[a]Single daily oral administration for 16 days

TABLE E

Cytoprotection Against ASA Lesions In Adjuvant Arthritis Study

| Group (mg/kg)[a] | No. of Rats with Lesions | Area of Lesion (mm²) Mean + S.E. | No. of Lesions Mean + S.E. |
|---|---|---|---|
| Controls | 1/10 | 0.04 ± 0.04 | 0.1 ± 0.1 |
| ASA 150 | 9/9 | 11.61 ± 4.42 | 25.7 ± 4.9 |
| TBPA 300 | 2/5 | 0.18 ± 0.15 | 1.0 ± 0.6 |
| ASA 150 + TBPA 300 | 5/5 | 5.28 ± 1.39 | 7.6* ± 2.2 |

*Significantly different from control; p ≦0.01
[a]Single daily oral administration for 16 days

EXAMPLE 3

Effect of Coadministration of 3,3'-Thiobis[propanoic Acid] With Aspirin On Acute Inflammation In Rats Male Sprague-Dawley rats (initial weight of about 200 g) received a single oral dose of TBPA at either 30, 100 or 300 mg/kg coadministered with 100 mg/kg of ASA in the carrageenin model of acute inflammation (paw edema) [C. A. Winler et al, "Carrageenin-Induced Edema in Hind Paw of the Rat as an Assay for Anti-Inflammatory Drugs, "Proc. Soc. Exptl. Biol. Med. 111, 544–547 (1962)] and it was found that this coadministration of TBPA with ASA did not appear to influence the anti-inflammatory efficacy of aspirin.

Results of these studies are given in Table F which also includes data for the standard phenylbutazone.

TABLE F

Effect of Coadministration of TBPA With ASA On Acute Inflammation In Rats

| Compound | Dose, mg/kg | Mean Paw Edema, ml + S.E. | % Inhibition |
|---|---|---|---|
| Control | | 1.12 ± 0.1 | |
| ASA | 100 | 0.67 ± 0.1 | 40* |
| TBPA + ASA | 300 100 | 0.74 ± 0.1 | 34* |
| Phenylbutazone | 100 | 0.70 ± 0.04 | 37* |

*Significantly different from control; p ≦0.01.
Number of rats per group were 9.

In another experiment using above said test procedure, TBPA at a dose of 300 mg/kg was found to produce no inhibition (0%), that is, it was found to have no anti-inflammatory activity.

EXAMPLE 4

Effect of Coadministration of 3,3'-Thiobis[propanoic Acid] With Aspirin On Chronic Inflammation In Rats Male Sprague-Dawley rats (initial weight of 225 to 250 g) received single oral daily doses of TBPA at either 150 or 300 mg/kg for 16 days either alone or coadministered with 150 mg/kg of ASA in said adjuvant-induced arthritis assay. It was found that TBPA did not demonstrate an effect on the development of arthritis and, also, that its coadministration with ASA did not influence the anti-inflammatory efficacy of ASA. Results of these studies are given below in Tables G and H.

TABLE G

Effect of Coadministration of TBPA With ASA On Adjuvant Arthritis In Rats

| Compound | Dose mg/kg | Injected Hind Paw Volume ml + S.E. | % Inhibition |
|---|---|---|---|
| Adjuvant Control | — | 5.57 ± 0.4 | — |
| Normal Control | — | 1.89 ± 0.03 | — |
| ASA | 150 | 3.31 ± 0.2 | 61* |
| TBPA | 150 | 5.14 ± 0.4 | 12 |
| TBPA + ASA | 150 150 | 3.76 ± 0.2 | 49* |

*Significantly different from control; p ≦0.01
Number rats per group were 9 or 10.

TABLE H

Affect of Coadministration of TBPA With ASA On Adjuvant Arthritis In Rats

| Compound | Dose mg/kg | Injected Hind Paw Volume ml + S.E. | % Inhibition |
|---|---|---|---|
| Adjuvant Control | — | 5.36 ± 0.4 | — |
| Normal Control | — | 1.87 ± 0.1 | — |
| ASA | 150 | 3.85 ± 0.3 | 43* |
| TBPA | 300 | 4.76 ± 0.5 | 17 |
| TBPA + ASA | 300 150 | 3.58 ± 0.2 | 51* |

*Significantly different from control; p ≦0.01
Number rats per group were 9 or 10.

EXAMPLE 5

Acute Toxicity of 3,3'-Thiobis[propanoic Acid] In Rats

TBPA was given as a single oral dose to male Sprague-Dawley rats to determine its approximate acute oral LD$_{50}$. The rats were fasted for four hours before medication, observed for seven days following medication and all surviving rats sacrificed and necropsied at the completion of the study. TBPA thus was found to have an ALD$_{50}$ of 6,000 mg/kg (7 days). This indicated a low order of acute toxicity although gastric irritancy was observed at this very high dose level.

EXAMPLE 6

Bioavailability of $^{14}$C-Aspirin In Rats Following Coadministration of 3,3'-Thiobis[propanoic Acid]

Sprague-Dawley male rats having initial body weights of 160–185 g received a single oral dose of $^{14}$C-aspirin at 100 mg/kg and displayed a blood radioactivity peak equivalent to 176±10.5 μg of ASA per ml at 1.6±0.32 hours postmedication. When TBPA (300 mg/kg) was administered 30 seconds prior to $^{14}$C-ASA (100 mg/kg), there was observed a blood radioactivity peak equivalent to 189±2.1 μg of aspirin per ml. at 2.3±0.29 hours postmedication. Nearly complete recovery of radioactivity was obtained in urine within 48 hours postmedication for all dose groups. In addition, 24 hour urinary metabolite profiles, as determined by gradient HPLC with radioactivity detection, were qualitatively similar among all dose groups. Thus, coadministration of TBPA at 300 mg/kg had no apparent effect on the bioavailability of $^{14}$C-ASA. The test results obtained are given in Tables I and J.

TABLE I

Recovery of Radioactivity In Urine Following Oral Administration of TBPA and $^{14}C$—ASA

| Time Period (hrs) | Percent of Dose (Mean ± S.E.)[a] TBPA | Control |
|---|---|---|
| 0–24 | 70.0 ± 10.6(N = 4) | 88.8 ± 5.1 |
| | 80.3 ± 3.8(N = 3)[b] | |
| 24–48 | 15.7 ± 4.7(N = 4) | 13.5 ± 1.7 |
| | 11.1 ± 1.4(N = 3)[b] | |
| 0–48 | 85.7 ± 6.7(N = 4) | 102 ± 6 |
| | 91.4 ± 5.0(N = 3)[b] | |

[a]Mean of four rats ± standard error.
[b]Mean values excluding one animal with urinary recovery of only 60%.

TABLE J

Mean Maximum Observed Aspirin Equivalent Concentration In Blood Following Administration of TBPA and $^{14}C$—ASA

| Cytoprotective Agent | $C_{max}$(eq. μg/ml ± S.E.)[a] | $T_{max}$(hr ± S.E.) |
|---|---|---|
| TBPA | 189 ± 2.1 | 2.3 ± 0.29 |
| Control | 176 ± 10.5 | 1.6 ± 0.32 |

[a]N = 4.

EXAMPLE 7

The compatibility and stability of mixtures of ASA and TBPA are illustrated by Examples 7–10.

Objective

To study the stability at 40° C./75% RH and 70° C. after one week of mixtures of ASA with TBPA and 80/20 ASA-starch granulation (ASA-SG) with TBPA.

Combinations (a) ASA 325 mg plus TBPA 325 mg.
(b) ASA 325 mg plus TBPA 50 mg.
(c) ASA-SG 406 mg plus TBPA 325 mg.
(d) ASA-SG 406 mg plus TBPA 50 mg.

Stress Conditions (a) 40° C./75% RH (relative humidity)
(b) 70° C.

Procedure of Preparation

All samples were prepared by grinding the combination in a mortar with pestle. Samples were well mixed, stored in amber glass vials with metal screw cap closures each having a pressure-sensitive ethyl vinyl acetate liner, and placed in the stress chambers. Samples were withdrawn for HPLC analysis after one week.

HPLC Assay

This method separates ASA and salicylic acid (SA) by high pressure liquid chromatography (HPLC). Sample mixtures are extracted with methanol, suitably diluted and chromatographed using the MCH-10 (Varian) 4.6×25 mm column. The mobile phase consists of 40% A and 60% B (A—0.02% phosphoric acid, B—methanol). The mobile phase was run at 2 ml/min and the UV detector was set at 285 NM. The retention time of ASA is 3.1 min. and that of SA acid is 5.3 min.

Results after one week:

| Combination (mg.) | Stress Temp. °C. | % ASA | % SA | Physical Appearance |
|---|---|---|---|---|
| Control (ASA) | 70 | 100 | none | no change |
| ASA325 + TBPA325 | 70 | 94.8 | 5.6 | white powder |
| ASA325 + TBPA50 | 70 | 98.5 | <1 | white powder |
| Control (ASA) | 40[a] | 98.8 | none | no change |
| ASA325 + TBPA325 | 40[a] | 97.9 | none | white powder |
| | | 99.0 | | |
| ASA325 + TBPA50 | 40[a] | 96.6 | none | white powder |
| Control (ASA-SG) | 70 | 99.9 | none | no change |
| ASA-SG406 + TBPA325 | 70 | 97.0 | <1 | no change |
| ASA-SG406 + TBPA50 | 70 | 99.1 | <1 | no change |
| Control (ASA-SG) | 40[a] | 101.6 | none | no change |
| ASA-SG406 + TBPA325 | 40[a] | 101.0 | none | no change |
| ASA-SG406 + TBPA50 | 40[a] | 101.7 | none | no change |

[a]At 75% relative humidity

EXAMPLE 8

Objective

Like that of Example 7 but determining ASA stability after two, three and seven weeks at 50° C.

Results after two weeks at 50° C.

| Combination (mg.) | Stress Temp. °C. | % ASA | % SA | Physical Appearance |
|---|---|---|---|---|
| Control (ASA) | 50 | 99.7 | none | no change |
| ASA325 + TBPA325 | 50 | 98.4 | none | no change, |
| | | 98.4 | | white powder |
| ASA325 + TBPA50 | 50 | 99.8 | none | no change, |
| | | 99.2 | | white powder |
| Control (ASA-SG) | 50 | 99.1 | none | no change |
| ASA-SG406 + TBPA325 | 50 | 98.7 | none | no change, |
| | | 98.1 | | white powder |
| ASA-SG406 + TBPA50 | 50 | >99 | none | no change, |
| | | >99 | | white powder |

When tested after three and seven weeks at 50° C., no changes in % ASA, % SA and physical appearance were found for any of the above combinations.

EXAMPLE 9

Objective

Like that of Example 7 but determining ASA stability after ten weeks at 25° C. and seven weeks at 50° C.

Results after ten weeks at 25° C.

| Combinations (mg) | Stress Temp. °C. | % ASA | % SA | Physical Change |
|---|---|---|---|---|
| Control (ASA) | 25 | >99 | 0 | none |
| ASA325 + TBPA325 | 25 | >99 | 0 | none |
| ASA325 + TBPA50 | 25 | >99 | 0 | none |
| Control (ASA-SG) | 25 | >99 | 0 | none |
| ASA-SG406 + TBPA325 | 25 | >99 | 0 | none |
| ASA-SG406 + TBPA50 | 25 | >99 | 0 | none |

Results after seven weeks at 50° C.

| Combinations (mg) | Stress Temp. °C. | % ASA | % SA | Physical Change |
|---|---|---|---|---|
| Control (ASA) | 50 | >99 | 0 | none |
| ASA325 + TBPA325 | 50 | >99 | 0 | none |
| ASA325 + TBPA50 | 50 | >99 | 0 | none |

EXAMPLE 10

Objective

Like that of Example 7 but determining ASA stability after three weeks at 40° C. (75% RH), 50° C. and 70° C.

Results after three weeks:

| Combinations | Stress Temp.°C. | % ASA | % SA | Physical Change |
|---|---|---|---|---|
| Control (ASA) | 40[a] | 100 | 0 | none |
| ASA325 + TBPA325 | 40[a] | 99.4 | 0 | none |
| ASA325 + TBPA50 | 40[a] | 100.1 | 0 | none |
| Control (ASA-SG) | 40[a] | 100.9 | 0 | none |
| ASA-SG406 + TBPA325 | 40[a] | 101.5 | 0 | none |
| ASA-SG406 + TBPA50 | 40[a] | 103.0 | 0 | none |
| Control (ASA) | 50 | 100.5 | 0 | none |
| ASA325 + TBPA325 | 50 | 99.8 | 0 | none |
| ASA325 + TBPA50 | 50 | 100.5 | 0 | none |
| Control (ASA-SG) | 50 | 99.5 | 0 | none |
| ASA-SG406 + TBPA325 | 50 | 100.7 | 0 | none |
| ASA-SG406 + TCBA50 | 50 | 101.0 | 0 | none |
| Control (ASA) | 70 | 98.9 | <1 | none |
| ASA325 + TBPA325 | 70 | 86.7 | 11.8 | none |
| ASA325 + TBPA50 | 70 | 93.7 | 3.2 | none |
| Control (ASA-SG) | 70 | 100.2 | <1 | none |
| ASA-SG406 + TBPA325 | 70 | 99.9 | 2.7 | none |
| ASA-SG406 + TBPA50 | 70 | 100.5 | 3.8 | none |

[a]At 75% relative humidity

EXAMPLE 11

Capsules containing various mixtures of ASA or ASA-starch granulation (ASA-SG) with TBPA are shown in Examples 11–14.

25 Capsules containing a 50:50 mixture of TBPA (325 mg) and ASA (325 mg) were prepared. The capsules were then assayed for ASA and free SA and the contents were examined to evaluate the compatibility of the two said ingredients.

| Formula | mg/capsule | × 30 capsules |
|---|---|---|
| 1. TBPA | 325 | 9.75 g |
| 2. ASA | 325 | 9.75 g |
| Capsule fill wt. | 650 | |
| Approx. empty cap. wt. | 120 | |
| Total filled cap. wt. | 770 | |

Procedure

1. Weigh ingredients 1 and 2.
2. Triturate each separately in a mortar to a fine particle size.
3. Combine the two, blending well.
4. Encapsulate into size OO capsules, with a target fill weight of 650 mg, each total filled capsule weighing approximately 770 mg. The actual weight range was from 768 to 805 mg, the average weight being 780 mg.
5. 25 capsules were filled, stored in a amber glass vial with metal screw cap closure having a pressure-sensitive ethyl vinyl acetate liner, kept at 25° C. for eight days, and then analyzed for aspirin and free salicylic acid by standard ultraviolet spectrometry [K. Kitamura et al, Chem. Pharm. Bull. 32 (4), 1484–1490 (1984)]

Analysis

After 8 days at 25° C., the quantity of ASA found per capsule by said standard ultraviolet spectrometric analytic procedure was 356.2, 356.2 and 365.0 mg. No SA acid was detected.

After 67 days at 25° C., the quantity of ASA found per capsule by said HPLC assay (Ex. 7) was 101.8% and no SA was detected.

EXAMPLE 12

The procedure of this example was like that of Example 11 but using 406 mg of an 80/20 ASA-starch granulation (containing 325 mg of ASA) in place of 325 mg of ASA.

| Formula | mg/capsule | × 30 capsules |
|---|---|---|
| 1. TBPA | 325 | 9.75 g |
| 2. 80/20 ASA-SG | 406 | 12.18 g |
| Capsule fill wt. | 731 | |
| Approx. empty cap. wt. | 125 | |
| Total filled cap. wt. | 856 | |

Procedure

1. Weigh both ingredients.
2. Triturate each ingredient separately in a mortar to a fine particle size.
3. Combine the two ingredients, blending well.
4. Encapsulate into size OO capsules, with a target fill weight of 731 mg and a total filled capsule weight of 856 mg. The actual weight range was from 847 to 883 mg, the average weight being 864 mg.
5. 25 capsules were filled, stored in a amber glass vial with metal screw cap closure having a pressure sensitive ethyl vinyl acetate liner, kept at 25° C. for seven days, and then analyzed as in Example 11.

Analysis

After 7 days at 25° C., the quantity of ASA found per capsule by said ultraviolet spectrometric procedure was 337.5, 337.5 and 337.5 mg. No SA was detected.

After 67 days at 25° C., the quantity of ASA found per capsule by HPLC assay was 100.6%, and no SA was detected.

EXAMPLE 13

This example was carried out following the procedure of Example 11 but using 50 mg instead of 325 mg of TBPA and using size 1 rather than size OO capsules.

| Formula | mg/capsule | × 30 capsules |
|---|---|---|
| 1. TBPA | 50 | 1.50 g |
| 2. ASA | 325 | 9.75 g |
| Capsule fill wt. | 375 | |
| Empty cap. wt. | 80 | |
| Total filled cap. wt. | 455 | |

There was thus obtained 25 filled capsules ranging in weight from 444 to 462 mg and averaging 453 mg. These were stored as in Example 11 at 25° C. for five days and analyzed.

Analysis

After 5 days at 25° C., the quantity of ASA found per capsule by said ultraviolet spectrometric procedure was 318.2, 321.3 and 321.3 mg., and no SA was detected.

After 67 days at 25° C., the quantity of ASA found per capsule by said HPLC assay was 98.8%, and no SA was detected.

EXAMPLE 14

This example was carried out following the procedure of Example 12 but using 50 mg instead of 325 mg of TBPA and using size O rather than OO capsules.

| Formula | mg/capsule | × 30 capsules |
|---|---|---|
| 1. TBPA | 50 | 1.50 g |
| 2. 80/20 ASA-SG | 406 | 12.18 g |
| Capsule fill wt. | 456 | |
| Empty cap. wt. | 80 | |
| Total filled cap. wt. | 536 | |

There was thus obtained 25 filled capsules ranging in weight from 542 to 564 mg and averaging 553 mg. These capsules were stored as in Example 11 at 25° C. for five days and analyzed.

Analysis

After 5 days at 25° C., the quantity of ASA found per capsule by said ultraviolet spectrometric procedure was 318.8, 331.3 and 328.8 mg, and no SA was detected.

After 67 days at 25° C., the quantity of ASA found per capsule by said HPLC assay was 99.0% and no SA was detected.

I claim:

1. The method of providing cytoprotection of the gastric mucosa in a mammal receiving aspirin perorally which comprises orally administering either prior to or in combination with aspirin a cytoprotectively effective amount of 3,3'-thiobis[propanoic acid], using at least about 1 part of 3,3'-thiobis[propanoic acid] per part by weight of aspirin.

2. The method according to claim 1 wherein the combination of aspirin and 3,3'-thiobis[propanoic acid] is administered in a pharmaceutically acceptable carrier.

3. The method according to claim 1 wherein aspirin and 3,3'-thiobis[propanoic acid] are administered in combination dosage form.

4. The method according to claim 1 wherein about 1 to about 3 parts by weight of 3,3'-thiobis[propanoic acid] per part of aspirin are administered in combination dosage form.

5. The method according to claim 1 wherein about equal parts by weight of 3,3'-thiobis[propanoic acid] and aspirin are administered in combination dosage form.

6. The method according to claim 1 wherein aspirin and 3,3'-thiobis[propanoic acid] are administered in separate dosage form.

7. The method of preventing or inhibiting gastric lesions in a mammal receiving aspirin perorally which comprises orally administering either prior to or in combination with aspirin a cytoprotectively effective amount of 3,3'-thiobis[propanoic acid], using at least about 1 part of 3,3'-thiobis[propanoic acid] per part by weight of aspirin.

8. The method according to claim 7 wherein the combination of aspirin and 3,3'-thiobis[propanoic acid] is administered in a pharmaceutically acceptable carrier.

9. The method according to claim 7 wherein aspirin and 3,3'-thiobis[propanoic acid] are administered in combination dosage form.

10. The method according to claim 7 wherein about 1 to about 3 parts by weight of 3,3'-thiobis[propanoic acid] per part of aspirin are administered in combination dosage form.

11. The method according to claim 7 wherein about equal parts by weight of 3,3'-thiobis[propanoic acid] and aspirin are administered in combination dosage form.

12. The method according to claim 7 wherein aspirin and 3,3'-thiobis[propanoic acid] are administered in separate dosage form.

13. A composition for providing cytoprotection of the gastric mucosa in a mammal receiving aspirin perorally which comprises aspirin in combination with a cytoprotectively effective amount of 3,3'-thiobis[propanoic acid], using at least about 1 part of 3,3'-thiobis[propanoic acid] per part by weight of aspirin.

14. A composition according to claim 13 comprising aspirin and 3,3'-thiobis[propanoic acid] in combination with a pharmaceutically acceptable carrier.

15. A composition according to claim 13 in unit dosage form comprising a mixture of aspirin and 3,3'-thiobis[propanoic acid] in a gelatin capsule.

16. A composition according to claim 13 in unit dosage form comprising a mixture of aspirin and 3,3'-thiobis[propanoic acid] in combination with a pharmaceutically acceptable excipient in a gelatin capsule.

17. A composition according to claim 13 in unit dosage tablet form comprising a mixture of aspirin and 3,3'-thiobis[propanoic acid] in combination with a pharmaceutically acceptable excipient.

18. A composition according to claim 13 comprising about 1 to about 3 parts by weight of 3,3'-thiobis[propanoic acid] per part of aspirin.

19. A composition according to claim 13 comprising about equal parts by weight of 3,3'-thiobis[propanoic acid] and aspirin.

* * * * *